United States Patent [19]

Dawans et al.

[11] 4,150,067
[45] Apr. 17, 1979

[54] METAL-CONTAINING POLYMERS, THEIR MANUFACTURE AND USE

[75] Inventors: François Dawans, Bougival; Didier Morel, Lilliers, both of France

[73] Assignee: Institut Francais du Petrole, Rueil-Malmaison, France

[21] Appl. No.: 847,630

[22] Filed: Nov. 1, 1977

Related U.S. Application Data

[62] Division of Ser. No. 657,144, Feb. 11, 1976, Pat. No. 4,080,490.

[30] Foreign Application Priority Data

Feb. 13, 1975 [FR] France .................. 75 04774

[51] Int. Cl.² .................. C08F 8/42; C08F 36/06; C08F 110/06; C08F 112/08
[52] U.S. Cl. .................. 260/878 R; 260/879; 260/884; 260/885; 260/886; 526/16; 526/48.1; 526/171; 526/240; 526/245; 526/249; 526/335; 526/346; 526/351
[58] Field of Search .................. 526/16, 48.1, 47.2; 260/878 R, 879, 884

[56] References Cited

U.S. PATENT DOCUMENTS

| | | | |
|---|---|---|---|
| 3,379,706 | 4/1968 | Wilke | 526/335 |
| 3,719,653 | 3/1973 | Dawans | 526/335 |
| 4,080,490 | 3/1978 | Dawans et al. | 528/48.1 |

*Primary Examiner*—William F. Hamrock
*Attorney, Agent, or Firm*—Millen & White

[57] ABSTRACT

Metal-containing polymers, particularly useful as catalysts for chemical reactions involving unsaturated hydrocarbon molecules, conform with the general formula:

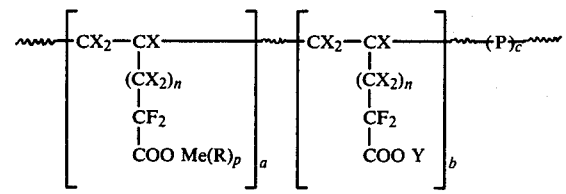

in which X is hydrogen, halogen or a monovalent hydrocarbon radical, n is 0 or an integer from 1 to 6, Me is a transition metal, each ligand R is selected from hydrogen, halogen, a hydrocarbon radical or a radical comprising a carboxy, carbonyl, amino, ether or phosphorus group, p is an integer from 1 to (m−1), m being the highest valency of said metal Me, Y is hydrogen, an alkali metal or a monovalent hydrocarbon radical, P is a unit derived from at least one polymerizable mono- or poly-functional vinyl monomer, and a, b and c are numbers such that, for a sum (a+b+c) of 100, (a+b) is from 1 to 100, a/(a+b) is from 0.1 to 1, and c is from 0 to 99.

7 Claims, No Drawings

METAL-CONTAINING POLYMERS, THEIR MANUFACTURE AND USE

This is a division, of application Ser. No. 657,144, filed Feb. 11, 1976.

This invention relates to new organo-metallic polymers and their manufacture. More particularly, the invention concerns polymeric products containing one or more metal derivatives linked to the polymer substrate through a fluorocarboxylic group and the use of these materials, particularly as catalysts.

A large variety of polymers containing carboxylic groups, as well as their salts, are already known; for example several patents have disclosed metal salts derived from polyacrylic acids, among which we can particularly mention U.S. Pat. No. 3,024,222 to Meyer L. Freedman and U.S. Pat. No. 3,779,952 to William J. Leonard.

Moreover, a number of metal catalysts deposited on, or associated with a polymeric carrier have been proposed (see for example, N. Kohler and F. Dawans in "Revue de l'Institut Francais du Pétrole", 27 No. 1 p. 105 (1972)). Among the organic polymeric carriers proposed in the prior art, those essentially used were polymers including groups having a well-defined electron donor property, such as amine, amide, phosphine or phosphite groups. However, such groups have the disadvantage of considerably reducing the activity of the catalyst in a number of reactions.

For this reason, there was an interest in the preparation of polymers including groups able to enhance the catalytic activity of the metal while maintaining ssaid metal strongly bound to the polymeric carrier, in order to avoid that the catalytic complex be liberated in the medium during the reaction.

It has been previously shown that, among the possible groups, halogenocarboxylic acids, and particularly fluoroacetic groups, were very convenient to enhance the activity of the metal catalysts; thus U.S. Pat. Nos. 3,660,445, 3,719,653 and 3,739,003 disclose transition metal halogenoacetate compounds having interesting catalytic properties.

It has now been discovered that polymers containing convenient fluorocarboxylic groups may be used as carriers for metal derivatives and lead in particular to the formation of very active catalysts for various reactions.

The organo-metallic polymers of the invention comply with the general formula:

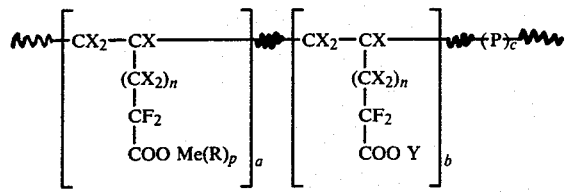

in which X is hydrogen, halogen (for example fluorine or chlorine) or a monovalent hydrocarbon radical, n is 0 or an integer from 1 to 6, Me is a transition metal, each ligand R is hydrogen, halogen, a hydrocarbon radical or a radical with a carboxy, carbonyl, amino, ether or phosphorus group, p is an integer from 1 to (m−1), m being the highest valency of said metal Me, Y is hydrogen, an alkali metal or a monovalent hydrocarbon radical, P is a unit derived from at least one polymerizable mono- or poly-functional vinyl monomer, and a, b and c are such that when their sum (a+b+c) is 100, (a+b) has a value from 1 to 100, preferably from 5 to 20, a/(a+b) ranging from 0.1 to 1, preferably from 0.2 to 1, and c has a value from 0 to 99, preferably from 80 to 95.

The term transition metal herein refers to a metal pertaining to one of groups IB, IVB to VIIB and VIII of the periodic table of the elements. By way of example of such metals there can be mentioned nickel, cobalt, iron, chromium, titanium, vanadium, molybdenum, tungsten, palladium and rhodium.

Generally, the average molecular weight, by weight, of the polymers or copolymers of the invention is higher than about 500, the upper limit of the molecular weight being not critical. However, organometallic polymers of the invention have, in most cases, an average molecular weight, by weight, from about 2,000 to 500,000.

Advantageously, at least one of the ligands R is a hydrocarbon radical of the π-allyl type, of the formula:

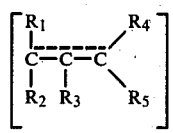

in which $R_1$ to $R_5$, identical or different, each represent a hydrogen atom or a monovalent hydrocarbon radical, for example an alkyl radical (particularly methyl). Radicals $R_1$ and $R_4$ may also be cyclized to a cyclic system with olefinic unsaturation, comprising for example from 5 to 8 carbon atoms, as for example the cyclopentenyl and cyclooctenyl systems.

The metal-containing polymers of the invention may be obtained by contacting a polymer or copolymer, optionally crosslinked, in which fluorocarboxylic groups are in the form of acids or esters, or even alkali metal salts, with at least one transition metal such as above defined or with at least one appropriate derivative of such a metal.

The polymers with fluorocarboxylic groups used for manufacturing the metal-containing polymers of the invention, essentially consist of polymers or copolymers derived from monomers having at least one 2,2-difluorocarboxylic group (in the form of an acid or ester or even of an alkali metal salt) and at least one polymerizable ethylenic bond such, for example, as a non-aromatic carbon-carbon double bond. The convenient monomers with a fluorocarboxylic group conform to the general formula $$CX_2=CX-(CX_2)_n-CF_2COO\,Y$$

in which X is a hydrogen atom, a halogen atom (preferably fluorine or chlorine) or a monovalent hydrocarbon radical, for example alkyl (particularly methyl), n is 0 or an integer from 1 to 6 (preferably 0, 1 or 2) and Y is hydrogen, an alkali metal or a monovalent hydrocarbon radical, for example an alkyl radical (particularly methyl or ethyl) or even an allyl radical. As examples of fluorocarboxylic monomers, there can be mentioned: 2,2-difluoro-5-hexenoic acid, perfluoro-3-butenoic acid, methyl perfluoro-3-butenoate, 2,2-difluoro-3,3-difluoro-4-pentenoic acid, ethyl 2,2-difluoro-3,3-dichloro-4-pentenoate, 2,2-difluoro-3-pentenoic acid and, preferably, 2,2-difluoro-3-butenoic acid or ethyl or allyl 2,2-difluro- 3-butenoate. A general method for manufacturing these monomers consists of telomerizing and hydrolizing convenient fluoro-halogenated derivatives, and then dehydrohalogenating the resulting product.

The polymers with fluorocarboxylic groups are prepared by polymerization of monomers such as above-defined, according to well-known techniques of the art, such for example as polymerization in solution in the presence of free-radical generators.

It is also possible to copolymerize the monomer having a fluorocarboxylic group with one or more polymerizable monomers having vinyl unsaturation, containing for example from 2 to 20 carbon atoms, such as ethylene, propylene, styrene, vinyl toluene, vinyl chloride, tetrafluoroethylene or methyl methacrylate. When it is desired to obtain a partially or completely cross-linked polymer, there will also be made use, as comonomers, of compounds containing several polymerizable ethylenic bonds, such for example as 1,3-butadiene, divinylbenzene or diallyl phthalate.

Moreover, an operating method, particularly adapted to the manufacture of copolymers comprising alkenyl fluorocarboxylate groups, for example allyl, methallyl or crotyl fluorocarboxylate groups, consists of copolymerizing the monomer comprising a fluorocarboxylic group in the form af an acid or ethyl ester with the vinyl (in most cases vinylaromatic) monomer; in the latter case, the ethyl ester groups of the copolymer are subsequently converted to acid groups. The copolymer in the acid form is then esterified with the convenient unsaturated alcohol.

Particularly interesting copolymers of the invention are those which have a molar content of from 1 to 40% of 2,2-difluoro-3-butenoic acid or the allyl ester thereof, from 60 to 99% of styrene and from 0 to 25% of divinylbenzene.

Other particularly interesting copolymers of the invention are produced by copolymerizing the fluorocarboxylic monomer with tetrafluoroethylene; they provide, after metallation, metal-containing fluorinated copolymers wich have various advantageous properties such as good thermostability, inertia with respect to chemical agents, improved adhesive properties and possibility of use in the form of a fine and porous powder.

During the synthesis of the copolymers, it is preferred to so select experimental conditions (for example respective concentrations of comonomer(s), sequential order of addition . . . ) that the fluorocarboxylic monomer properly distributes, for example in a statistical manner, among the units forming the polymer chain; this will subsequently result in preventing local high metal concentrations.

For manufacturing the organo-metallic polymers of the invention, the polymer with fluorocarboxylic groups, as above-defined, is contacted with at least one transition metal in its metal form (preferably in a finely divided state), in the hydride form, in the form of ions, as for example in the anhydrous salts, or even in the form of an organometallic derivative. In said case, the preference is given to carbonyl metals and to organometallic compounds having a good solubility in a hydrocarbon phase, and a substantial reactivity with respect to the fluorocarboxylic groups. Non-limitative examples of such compounds are: bis cyclooctadiene nickel, dodecatrienediyl nickel, cyclododecatriene nickel, bis cyclopentadiene cobalt, hexacarbonyl iron, bis benzene chromium, tris allyl chromium, tetramethyl titanium, cyclopentadiene tetracarbonyl vanadium, hexacarbonyl molybdenum, benzene tricarbonyl molybdenum, tricarbonyl cyclopentadiene tungsten hydride or bis crotyl palladium.

The contact of the polymer having fluorocarboxylic groups with the metal may be conducted in homogeneous phase or heterogeneous phase, generally in a non-aqueous medium which is inert with respect to the metal compound.

When conducting the reaction in homogeneous phase, the polymer is preliminarily dissolved in a hydrocarbon solvent, for example an aromatic solvent such as benzene, toluene or orthodichlorobenzene, or in a polar solvent, for example an ether such as tetrahydrofuran or dioxane. The metal compound is also dissolved in an appropriate inert solvent such as an aliphatic or aromatic hydrocarbon, an ether or a ketone. When using different media for dissolving the polymer and the metal compound, it is essential to select the two solvents in such a manner that none of them would produce the precipitation of one of the reactants.

The reaction may also be conducted in heterogeneous phase by contacting either a polymer in solution with a suspension of a metal compound or a suspensiobn or a gel of polymer with a solution containing the metal, or the polymer with the metal compound in suspension; however, the latter method is generally less convenient for accurately controlling the reaction of metal grafting on the polymer.

When using cross-linked polymers in the form of powder, fiber, film or pulp, the preferred ones are the porous products whose specific surface is higher than 1 $m^2/g$, preferably from 20 to 200 $m^2/g$. There can also advantageously be used polymers cross-linked to a small extent (for example with a divinylbenzene content lower than 15 moles %) and in the form of a swollen gel in a preferably polar, hydrocarbon phase, whereby it is possible to attain still higher specific surfaces, for example of about 2000 $m^2/g$.

Preferably, the polymer with fluorocarboxylic groups is contacted with the metal at a moderate temperature, for example from $-20°$ to $50°$ C.; however, depending on the nature of the metal compound involved, it is also possible to proceed at a higher temperature, for example $150°$ C. or more.

The contact time is variable and depends on the experimental conditions and the desired metal content in the produced polymer; generally it is from 0.1 to 20 hours.

Similarly, the respective concentrations of polymer and of metal may be varied in large proportions. For example, there can be used from 0.1 to 5 metal g-atoms per fluorocarboxylic equivalent. Generally, it is preferred to use concentrations from 0.5 to 2 metal g-atoms per fluorocarboxylic equivalent. The polymers obtained in these conditions contain from 0.1 to 1 and preferably from 0.2 to 1 metal g-atom per fluorocarboxylic equivalent.

The new organometallic polymers of the invention may be advantageously used in various applications; by way of illustration we can mention their use as grafting substrate, as metal finish, for example to insure a better adherence between a polymer matrix and mineral fillers, or even in the field of magnetic paints and plastics. They are also particularly convenient for the manufacture of coatings with biocidic properties, used for example for coating underground cables, since the toxic agent, such as carbonyl metal derivative, is liable to a lesser extent to diffuse during time. There can also be used certain metallic polymers of the invention, such as ferrocene derivatives, as antiphotodegradating agent, for example to improve the resistance to ageing of paints exposed to the sun.

In addition, the polymers of the invention are particularly advantageous as catalysts in chemical reactions, since they have the essential characteristic of containing one or more metals linked to the chain through a fluorocarboxylate group. Depending on the cross-linking degree of the polymer substrate and on the nature of the reaction medium, there can be obtained supported homogeneous or heterogeneous catalysts, convenient for various reactions such as hydrogenation, isomerization, oligomerization, polymerization or carbonylation of unsaturated hydrocarbon molecules. The use of metal-containing polymers of the invention, in the form of a swollen gel in the reaction medium is especially advantageous, since it has the the usual high specificity of catalysts in the homogeneous phase, while also having the benefit of the qualities of the catalysts in heterogeneous phase with respect to the ease of separation and recovery from the reaction products, for example by decantation, centrifugation or filtration, as well as the capability of recycling the catalyst for several successive operations without substantial loss of activity.

Without departing from the scope of the invention, there can be used, as catalysts, products obtained by contacting organometallic polymers of the invention with various co-catalysts, depending on the reaction to be catalyzed.

Among these co-catalysts, there can be mentioned:
—those which have the properties of LEWIS acids or BRONSTED acids, for example boron trifluoride, titanium tetrachloride, aluminum bromide, ethylaluminum dichloride or hydrofluoric acid;
—those which have electron-acceptor properties, for example halogenated quinones or halogeno-acetic acids;
—or also those which have reducing properties, for example tri-isobutyl aluminum, diethyl aluminum monochloride, butyl lithium or lithium aluminum hydride.

The following non-limitative examples illustrate the invention and give more precise details of experimentation; more particularly example 1 describes the preparation of a monomer with ethylenic unsaturation, containing a difluorocarboxylic group; examples 2 to 4 illustrate the synthesis of various polymers containing at least one difluorocarboxylic substituent; examples 5 to 7 describe the preparation of polymers containing a metal; and finally, examples 8 to 14 illustrate the use of the obtained polymers as supported catalysts.

EXAMPLE 1

An amount of 340 g of chlorotrifluoroethylene is treated at room temperature and under ultraviolet radiation with 467 g of bromine; the reaction mixture is then distilled and there is recovered, at 91°–92° C., 807 g of 1,1,2-trifluoro-2-chloro-1,2-dibromoethane, $Br\ CF_2CFCl\ Br$. This compound, in an amount of 500 g, is heated at 80° C. during 16 hours in the presence of oleum and mercury oxide; the gas which evolves is collected in ethanol. By distillation of the organic phase, there is recovered, at 109°–110° C., 293 g of ethyl bromodifluoroacetate, $Br\ CF_2CO_2C_2H_5$. 165 g of this compound is telomerized at 95° C., in the presence of 2.37 g of benzoyl peroxide and under an ethylene pressure of 3.5 atmosphere. The reaction product is fractionated under reduced pressure; there is recovered, at 65°–67° C., under 3.5 mm Hg, 100 g of ethyl 4-bromo-2,2-difluorobutanoate, $Br\ (CH_2)_2CF_2CO_2C_2H_5$, which is finally dehydrohalogenated in the presence of sodium ethylate. By this way, there is obtained 52 g of ethyl 2,2-difluoro-3-butenoate. $CH_2=CH-CF_2-CO_2C_2H_5$. The total conversion of chlorotrifluoroethylene to unsaturated carboxylic ester is 80%.

EXAMPLE 2

A mixture of 15 g of ethyl 2,2-difluoro-3-butenoate (0.1 mole) and 10.4 g of styrene (0.1 mole) in solution in 130 cc of toluene is stirred at 80° C. for 70 hours, in the presence of 0.72 g of benzoyl peroxide.

The produced copolymer is separated from the reaction medium by precipitation in an excess of methyl alcohol and it is dried under reduced pressure up to constant weight. There is obtained 16.7 g of a polymer having an average molecular weight, by weight, of 17,000 and containing 92 moles % of styrene and 8 moles % of fluorinated ester. 8 g of this copolymer is redissolved into 50 cc of a dioxane-water mixture, and hydrolized in the presence of 0.5 g of sulfuric acid; there is thus obtained 7.8 g of a copolymer containing 8 moles % of 2,2-difluorobutenoic acid. The various recurring units forming the polymer may be represented as follows:

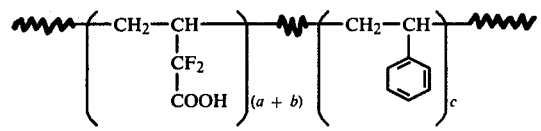

For a sum (a+b+c) equal to 100, the values of (a+b) and c are respectively 8 and 92.

EXAMPLE 3

11 g of a copolymer containing 85 moles % of styrene and 15 moles % of 2,2-difluoro-5-hexenoic acid, prepared in conditions similar to those of example 2, is dissolved in 100 cc of benzene; the solution is heated to reflux for 16 hours in the presence of 5.7 g of allyl alcohol. The water formed during the esterification is eliminated in the form of an azeotrope distilling at 69.4° C. under 760 mm Hg, and the reaction product is separated by lyophylization of benzene.

There is thus obtained 11.5 g a polymer which, according to spectral analysis conducted by infrared spectrometry and by nuclear magnetic resonance, appears as constituted of 85 moles % of styrene, 2 moles % of fluorocarboxylic acid and 13 moles % of allyl ester. Thus, it can be represented as follows:

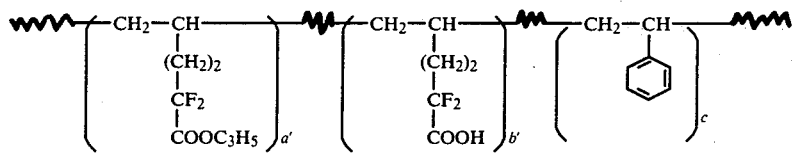

For a sum (a'+b'+c) of 100, the values of a', b' and c are respectively 13; 2 and 85.

EXAMPLE 4

A solution of 3.3 g of 2,2-difluoro-3,3-difluoro-4-pentenoic acid (0.0165 mole) prepared according to the general process described in example 1, 7 g of styrene (0.067 mole) and 1.2 g of divinyl benzene (0.009 mole) in 20 cc of toluene, is stirred at 130° C. for 4 hours in the presence of 0.2 g of ditertiobutyl peroxide. A gel is progressively formed during the reaction; at the end of the reaction, the insoluble fraction is separated by centrifugation or filtration and washed repeatedly with petroleum ether. The determination of the carboxylic groups, carried out by titration, with potash, of the gel swollen in dioxane, in the presence of bromothymol blue, indicates an acid content of about 0.5 mole per gram of terpolymer.

The weight of recovered polymer after drying of the gel is 7 g.

The cross-linked polymer, thus obtained, swells in various media, without being dissolved.

It contains units of the formulas:

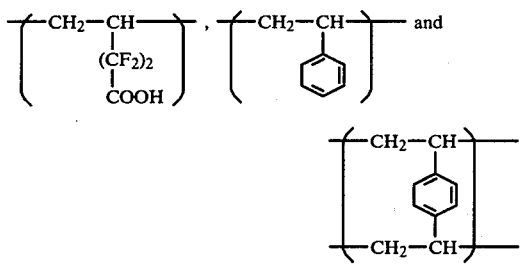

EXAMPLE 5

A solution of 10 g of the polymer of example 2 (corresponding to 7.4 fluorocarboxylic milliequivalents) in 100 cc of benzene is contacted, at room temperature, with a solution of 2.11 g of biscyclooctadiene nickel $(C_8H_{12})_2$ Ni (corresponding to 7.4 nickel milli-gram-atoms) in 50 cc of benzene, yielding accordingly 1 nickel g-atom per fluorocarboxylic equivalent. The mixture is stirred for 1 hour and it progressively turns to a yellow-orange color. The benzene and cyclooctadiene liberated during the reaction are then removed by evaporation under reduced pressure. There is thus obtained 10.4 g of a colored powder, soluble in the aromatic hydrocarbon phase; the nickel content of the polymer is 3.9% by weight (which corresponds to 0.93 g- at. of Ni per fluorocarboxylic equivalent) and the nuclear magnetic resonance spectrum of a polymer solution in benzene shows the presence of bonds of the π-allyl type; the probable structure of the complex formed between the metal and the polymer is accordingly the following:

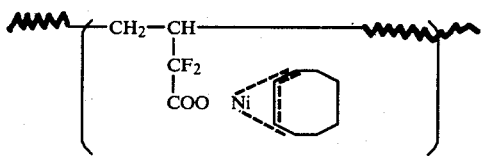

EXAMPLE 6

10 g of the polymer of example 3 (13.5 fluorocarboxylic milliequivalents) is dissolved in 100 cc of anhydrous 1,2-dimethoxyethane; 3.12 g of hexacarbonyl molybdenum, $Mo(CO)_6$ (11.8 Mo millig-at.) is added thereto. The reaction mixture is stirred at 85° C. for 16 hours and a slight stream of argon is passed thereon for carrying away the carbon monooxide evolved during the reaction. The solution progressively turns red; at the end of the reaction, an excess of petroleum ether is added in order to precipitate the polymer which is separated by filtration, washed and dried under reduced pressure up to constant weight. The resulting polymer contains 10.2% by weight of molybdenum (0.9 g-at. of Mo per fluorocarboxylic equivalent) and the spectral methods (IR and NMR) indicate that the polymer contains units having the following structure:

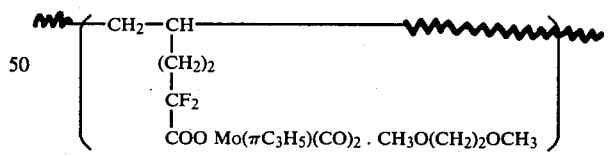

EXAMPLE 7

20 g (10 fluorocarboxylic milliequivalents) of the polymer of example 4 is swollen in 250 cc of toluene; 0.58 g (10 milli-g at.) of nickel in the form of 2,6,10-dodeca-triene-1,12-diyl nickel, in solution in toluene, is added and the mixture is stirred at 20° C. for 30 minutes. The polymer gel, which turned to a red-orange color, is then decanted under inert atmosphere and washed repeatedly with benzene. It contains 2 g. of nickel per 100 g of polymer (0.7 g-at. of nickel per fluorocarboxylic equivalent) and the nickel is attached to the polymeric substrate, likely through a π-allyl complex of the following type:

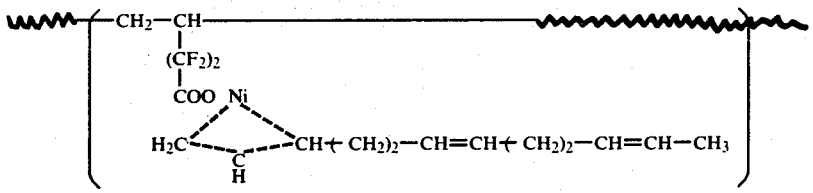

EXAMPLE 8

4.5 g of the polymer of example 5 is added to a solution of 45 g of styrene in 50 cc of ortho dichlorobenzene, in order to obtain a nickel concentration of $3\times10^{-2}$ g-atom per liter of reaction solution. The mixture, after stirring for 30 minutes at 50° C., is distilled under reduced pressure up to obtainment of a dry product. By fractionation of the distillate, there is obtained 40 g of a styrene dimer, trans 1,3-diphenyl-1-butene (boiling point = 118±2° C. under 7 mm Hg). To the solid residue from the distillation, there is again added a solution of 45 g of styrene in 50 cc of orthodichlorobenzene and the process is conducted as previously with this new reactant feed; there is obtained, by this way, 38 g of 1,3-diphenyl-1-butene. In this manner, the nickel containing polymer may be recycled several times during the process of styrene catalytic dimerization.

By way of comparison, when using nickel at the same initial concentration, in the form of a complex not associated to a polymer, in the considered case, bis ($\pi$-allyl nickel trifluoracetate),

[$\pi$—C$_3$H$_5$Ni OOCCF$_3$]$_2$.

there is obtained, in the same experimental conditions, 42.7 g of 1,3-diphenyl-1-butene, but the catalyst residue, after distillation, no longer shows an activity when adding thereto a new styrene feed.

EXAMPLE 9

$2.5\times10^{-2}$ mole of triethyl aluminum Al(C$_2$H$_5$)$_3$, is added to 300 cc of a solution in cyclohexane containing $10^{-2}$ molybdenum g-atom in the form of the polymer of example 6; the mixture is stirred and heated to 90° C. Then 130 g of methyl 2,4-hexadiene oate (or methyl sorbate) is added and the hydrogen pressure is maintained at 25 atm.. After 4 hours of reaction at 120° C., there is obtained a 94% conversion to methyl 4-hexene oate; this result is thus different from those obtained with catalytic complexes of the same type but not supported by a polymer according to this invention (see, for example, E. N. Frankel et al. in Journal of Organic Chemistry 34 p. 3930, 3936 (1969)), which generally result in the 1,4-addition of hydrogen and consequently in the formation of methyl 3-hexene oate.

EXAMPLE 10

5.4 g of 1,3-butadiene is added to a suspension of 5.8 g of the polymer of example 7 in 25 cc of toluene, which corresponds to respective nickel and butadiene concentrations of $2\times10^{-2}$ g-atom and 4 moles per liter of solution. The mixture is stirred for 3 hours at 50° C.; the phase in solution is then decanted and the solvent distilled and recycled to the insoluble phase. By this way, there can be separated 4.8 g of polybutadiene containing more than 90% of 1,4 cis units and whose nickel content is lower than 20 ppm. The insoluble phase containing the catalyst may be reused for initiating a new polymerization reaction; after 5 cycles, the loss of activity of the supported catalyst of the invention is about 20% of its initial activity.

EXAMPLE 11

To $1.2\times10^{-3}$ molybdenum g-atom in the form of the polymer as prepared in example 6, there is added 450 cc of benzene and 50 cc of 1,3-butadiene. The mixture is stirred and heated to 40° C. for 7 hours. After decantation of the catalyst, a viscous solution of polybutadiene is recovered. It contains 7 ppm of molybdenum and the microstructure of the polybutadiene, obtained with a conversion rate of 85%, is as follows: 80% of 1,2 units, 16% of 1,4 cis units and 4% of 1,4-trans units.

The polymerization may be performed again by using the catalyst residue, everything else being unchanged. In this case, there is obtained solutions of polybutadiene containing less than 1 ppm of molybdenum and the microstructure of the produced polymer is identical to that obtained during the first operation.

EXAMPLE 12

$10^{-2}$ mole of triethylaluminum Al(C$_2$H$_5$)$_3$ is added to $3.3\times10^{-3}$ nickel g-atom in the form of the polymer of example 7 swollen in 200 cc of benzene. This mixture is stirred under hydrogen pressure at 25° C. for 1 hour. A solution of 100 cc of cyclopentadiene, freshly prepared in 300 cc of benzene, is added thereto and the resulting mixture is stirred at 30° C., while maintaining a constant hydrogen pressure of 5 at. After 50 minutes of reaction, 95% by mole of cyclopentadiene has been converted to cyclopentene (80%) and cyclopentane (15%). A quantitative conversion of cyclopentadiene to cyclopentane is obtained after 130 minutes of reaction.

After decantation of the catalyst, the solution withdrawn is free of nickel and aluminum.

To the catalyst residue there is added a new reaction feed, i.e. a solution of 100 cc of cyclopentadiene in 400 cc of benzene; the hydrogenation is conducted under the same conditions as precedingly.

By this way, it has been possible to perform 8 successive hydrogenations without observing any loss of catalyst activity and without requiring any addition of organoaluminum compound.

EXAMPLE 13

To $2.2\times10^{-3}$ nickel g-atom in the form of the polymer of example 7, there is added $4\times10^{-2}$ mole of dichloromonoethyl aluminum, C$_2$H$_5$AlCl$_2$, and 1 liter of liquid propylene. The mixture is stirred at 15° C. for 6 hours. The catalyst is then decanted and the unconverted propylene is evaporated: there is obtained 300 cc of a solution which is then hydrogenated in order to be more easily analyzed by gas-chromatography. The resulting solution contains 1.8% by mole of dimethylbutane, 66.3% by mole of methylpentanes and 31.9% by mole or normal hexane.

EXAMPLE 14

Example 13 is repeated but with a solution of 200 cc of propylene in 300 cc of chlorobenzene, everything else being unchanged.

After 4 hours of reaction, propylene has been entirely converted; the composition of dimerization product, separated after decantation of the catalyst, is identical to that obtained in example 13.

The same reaction has been repeated twice by using the catalyst residue and without observing any loss of activity of the catalyst and without requiring any addition of organoaluminum compound.

The expression "equivalent" or "milli equivalent", as used in this specification, must be understood as "gram-equivalent" or "milli-gramequivalent", respectively.

What we claim is:

1. A process which comprises oligomerizing or polymerizing an ethylenically unsaturated hydrocarbon in the presence of a catalyst, said catalyst being (I) an organometallic polymer consisting essentially of a proportion a of recurring units (A) of the general formula

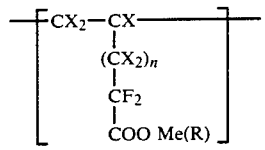

a proportion b of recurring units (B) of the general formula

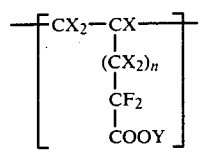

and a proportion c of recurring units —[P]—, wherein n is 0 or an integer from 1 to 6; X is a hydrogen atom, or a chlorine or a fluorine atom; Me is nickel, cobalt or iron; R is a $\pi$-allylic hydrocarbon ligand of the formula

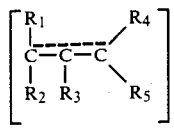

in which each of radicals $R_1$ to $R_5$ is a hydrogen atom or a monovalent hydrocarbon radical, or $R_1$ and $R_4$ connect to form a carbocyclic ring; Y is a hydrogen atom or an allyl radical; and P is a unit derived from at least one vinylaromatic hydrocarbon; and a, b and c are such numbers that, for a sum (a+b+c) of 100, (a+b) is from 5 to 20, with a/(a+b) from 0.1 to 1, and c is from 95 to 80, or (II) an organometallic polymer consisting essentially of a proportion a of recurring units (A) of the general formula

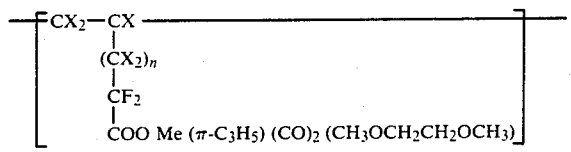

a proportion b of recurring units (B) of the general formula

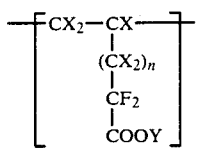

and a proportion c of recurring units —[P]—, wherein n is 0 or an integer from 1 to 6 inclusive; X is a hydrogen atom, or a chlorine or a fluorine atom; Me is molybdenum or tungsten; Y is a hydrogen atom or an allyl radical;

and P is a unit derived from at least one vinylaromatic hydrocarbon; and a, b and c are such numbers that, for a sum (a+b+c) of 100, (a+b) is from 5 to 20, with a/(a+b) from 0.1 to 1, and c is from 95 to 80, or an organometallic polymer of the general formula

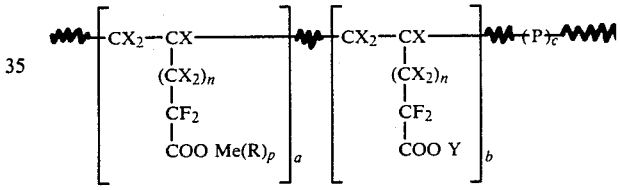

in which X is hydrogen, halogen or monovalent hydrocarbon radical, n is 0 or an integer from 1 to 6 inclusive, Me is a transition metal selected from nickel, cobalt, iron, chromium, titanium, vanadium, molybdenum, tungsten, palladium or rhodium, each ligand R is selected from hydrogen, halogen, a hydrocarbon radical, or a radical comprising carbonyl and ether, p is an integer from 1 to (m−1), m being the highest valency of said metal Me, Y is hydrogen, an alkali metal or a monovalent hydrocarbon radical, P is a unit derived from at least one polymerizable mono- or poly-olefinic vinyl aromatic hydrocarbon monomer, and a, b and c are numbers such that, for a sum (a+b+c) of 100, (a+b) is from 5 to 20, a/(a+b) is from 0.1 to 1, and c is from 95 to 80.

2. A process according to claim 1, comprising the polymerization of butadiene-1,3.

3. A process according to claim 1, comprising the dimerization of propylene.

4. A process according to claim 1, comprising the dimerization of styrene.

5. A process according to claim 2, wherein the catalyst is a polymer containing units having the following structure

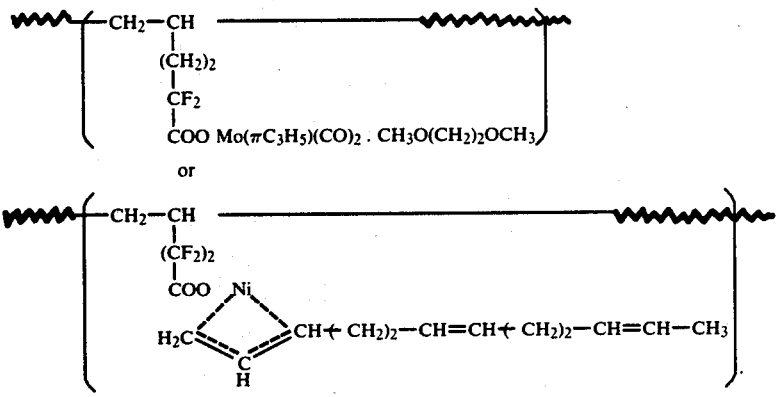
6. A process according to claim 3, wherein the catalyst is a polymer having units of the following structure
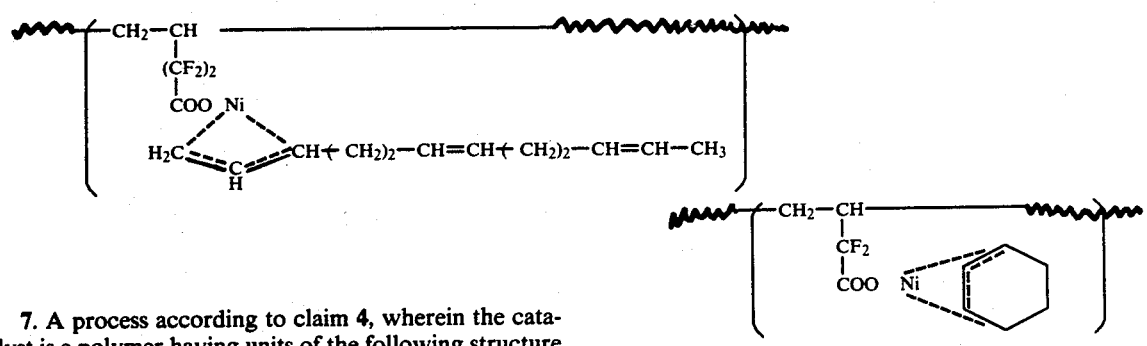
7. A process according to claim 4, wherein the catalyst is a polymer having units of the following structure